US012773393B2

(12) United States Patent
Koutnikova et al.

(10) Patent No.: US 12,773,393 B2
(45) Date of Patent: Oct. 27, 2026

(54) COMPOSITION FOR REDUCING HEPATIC TRIGLYCERIDES AND/OR IMPROVING GLUCOSE METABOLISM

(71) Applicants: Compagnie Gervais Danone, Paris (FR); Universite Laval, Québec (CA)

(72) Inventors: Hana Koutnikova, Gif sur Yvette (FR); André Marette, Levis (CA)

(73) Assignees: Compagnie Gervais Danone, Paris (FR); Universite Laval, Québec (CA)

( * ) Notice: Subject to any disclaimer, the term of this patent is extended or adjusted under 35 U.S.C. 154(b) by 733 days.

(21) Appl. No.: 17/997,056

(22) PCT Filed: Apr. 27, 2021

(86) PCT No.: PCT/IB2021/000311

§ 371 (c)(1),
(2) Date: Oct. 25, 2022

(87) PCT Pub. No.: WO2021/220059

PCT Pub. Date: Nov. 4, 2021

(65) Prior Publication Data

US 2023/0165818 A1 Jun. 1, 2023

Related U.S. Application Data

(60) Provisional application No. 63/015,872, filed on Apr. 27, 2020.

(51) Int. Cl.

| | |
|---|---|
| ***A61K 31/19*** | (2006.01) |
| ***A23C 9/123*** | (2006.01) |
| ***A23L 33/175*** | (2016.01) |
| ***A61P 1/16*** | (2006.01) |
| ***A61P 3/06*** | (2006.01) |
| ***A61P 3/10*** | (2006.01) |

(52) U.S. Cl.

CPC .............. *A61K 31/19* (2013.01); *A23C 9/123* (2013.01); *A23L 33/175* (2016.08); *A61P 1/16* (2018.01); *A61P 3/06* (2018.01); *A61P 3/10* (2018.01)

(58) Field of Classification Search

CPC ...................................................... A61K 31/19

See application file for complete search history.

(56) References Cited

U.S. PATENT DOCUMENTS

2015/0025143 A1* 1/2015 Sathyavageeswaran .................... A61P 31/10 514/557

FOREIGN PATENT DOCUMENTS

| | | | | |
|---|---|---|---|---|
| CA | 2598786 A1 | | 12/2008 | |
| WO | 2014078459 A1 | | 5/2014 | |
| WO | 2014094279 A1 | | 6/2014 | |
| WO | WO2014/094279 | * | 6/2014 | ............. A61K 31/26 |
| WO | 2015052086 A1 | | 4/2015 | |
| WO | WO2015/052086 | * | 4/2015 | ............. A61K 31/26 |

OTHER PUBLICATIONS

Pakiet et al., Obesity Surgery (2020) vol. 30 pp. 304-312.*
Mardinoglu et al., EBioMedicine (2018) pp. 151-155.*
Jang et al., Nat Med. (2016) vol. 22(4) pp. 421-426.*
Pakiet et al., "The Effect of One Anastomosis Gastric Bypass on Branched-Chain Fatty Acid and Branched-Chain Amino Acid Metabolism in Subjects with Morbid Obesity", Aug. 22, 2019, vol. 30, No. 1, p. 304-312.
Mardinoglu et al., "Elevated Plasma Levels of 3-Hydroxyisobutyric Acid Are Associated With Incident Type 2 Diabetes", NL, Dec. 7, 2017, vol. 27, p. 151-155, Retrieved from the Internet: URL:www.ncbi.nlm.nih.gov/pmc/articles/PMC5828558/pdf/main.pdf.
Jang et al., "A branched-chain amino acid metabolite drives vascular fatty acid transport and causes insulin resistance", New York, Apr. 1, 2016, vol. 22, No. 4, p. 421-426, Retrieved from the Internet: URL: www.ncbi.nlm.nih.gov/pmc/articles/PMC4949205/pdf/nihms758301.pdf.
International Search Report and Written Opinion mailed, Sep. 2, 2021, for PCT/IB2021/000311.

* cited by examiner

*Primary Examiner* — Paul V Ward
(74) *Attorney, Agent, or Firm* — ArentFox Schiff LLP

(57) ABSTRACT

The present invention relates to a composition comprising branched chain amino acid metabolites for use in reducing hepatic triglycerides and/or improving glucose metabolism in an individual.

10 Claims, 3 Drawing Sheets

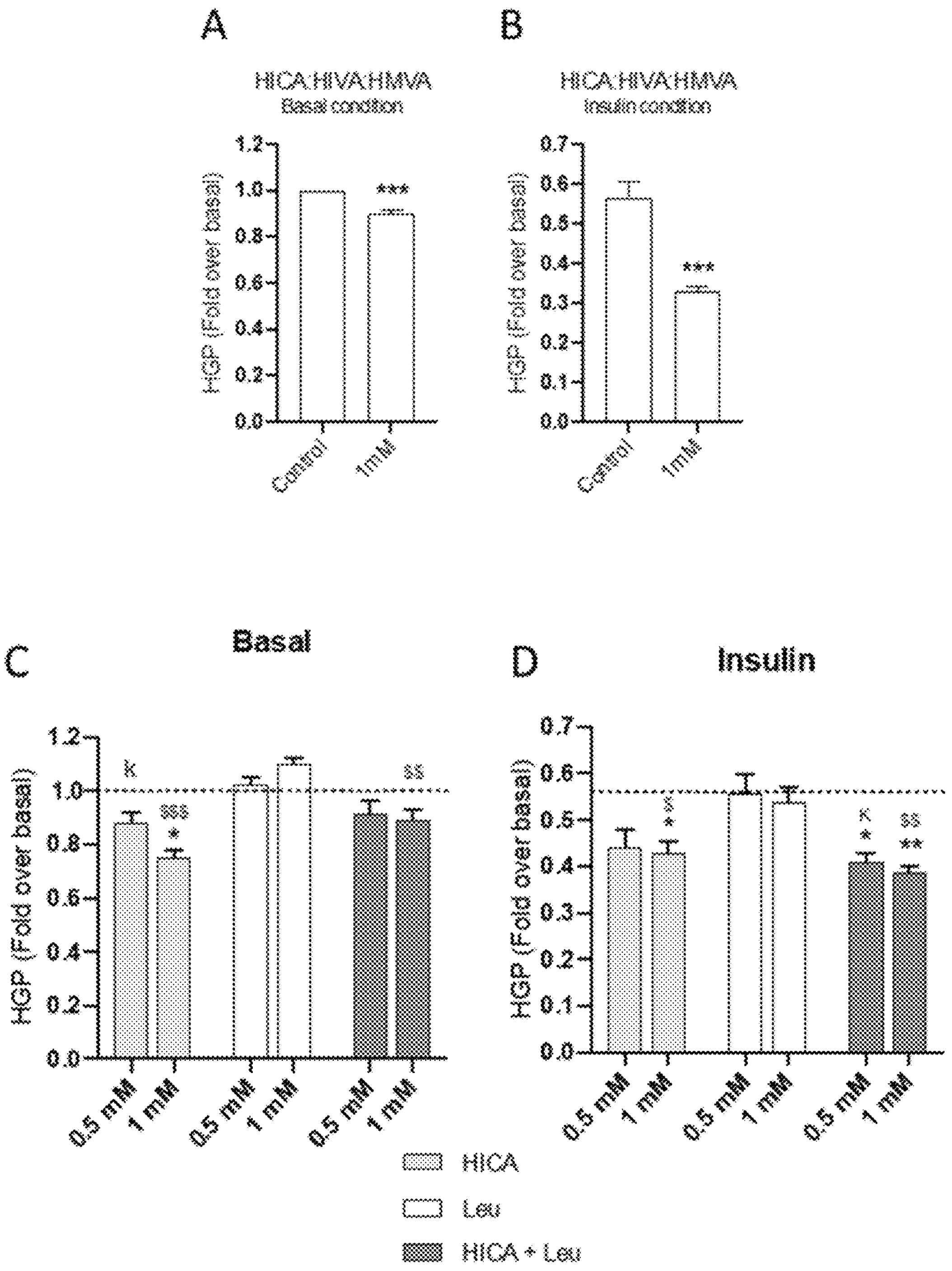
FIGURE 2 (start)

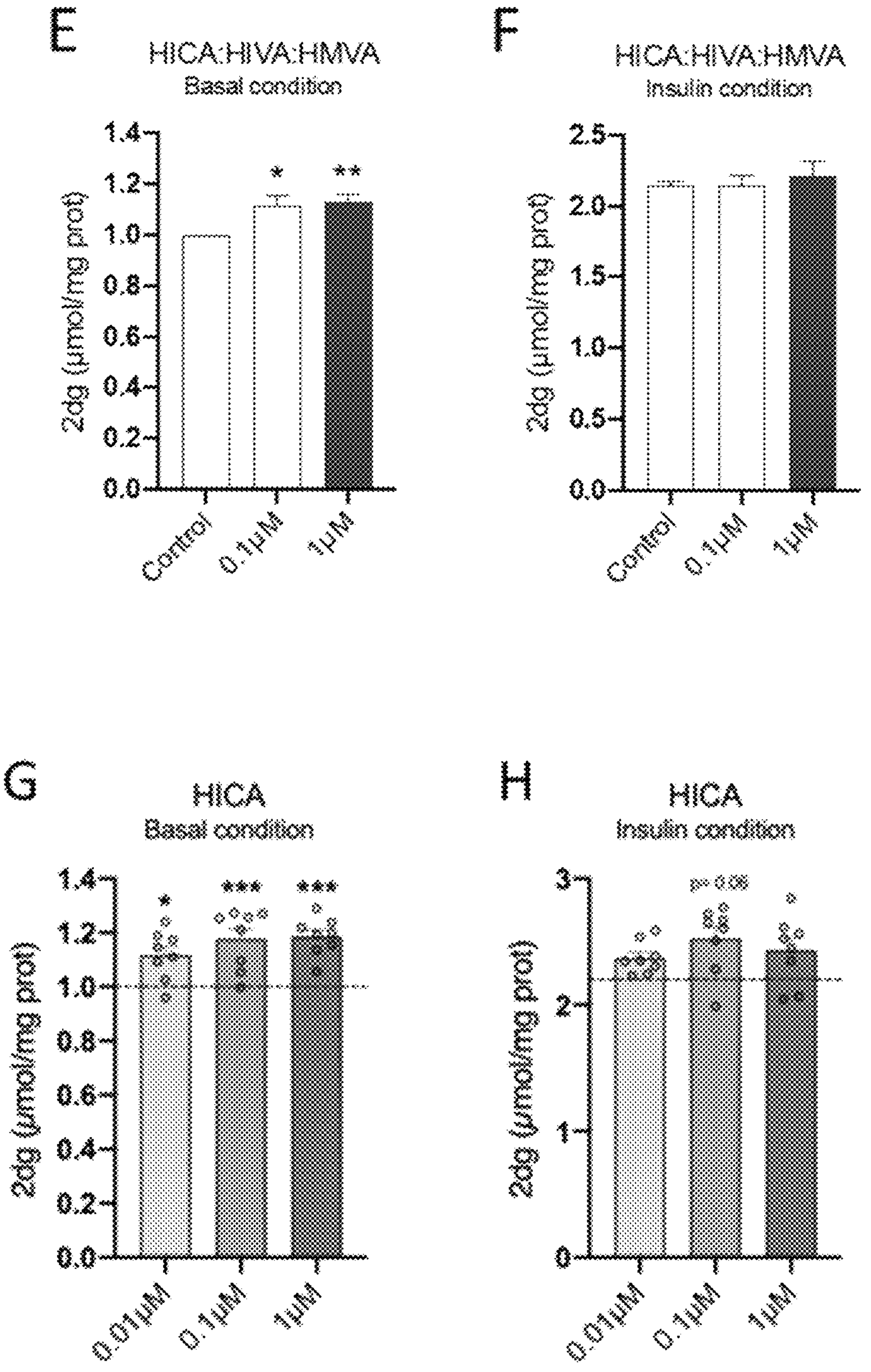
FIGURE 2 (end)

COMPOSITION FOR REDUCING HEPATIC TRIGLYCERIDES AND/OR IMPROVING GLUCOSE METABOLISM

CROSS-REFERENCE TO RELATED APPLICATIONS

This application is a National Phase of PCT Application No. PCT/IB2021/000311, filed Apr. 27, 2021, which claims the benefit of U.S. Application No. 63/015,872, filed Apr. 27, 2020, the disclosures of each of which are hereby incorporated by reference in their entireties.

FIELD OF THE INVENTION

The present invention relates to a composition for use in reducing hepatic triglycerides and/or improving glucose metabolism in an individual.

TECHNICAL BACKGROUND

Type 2 diabetes (T2D) is a disease characterized by the fact that insulin fails to properly metabolize glucose because of abnormal glucose uptake by skeletal muscle and impaired suppression of blood sugar production by the liver while paradoxically allowing the accumulation of hepatic triglycerides. This combination results in multiple health risks and disorders, including high blood sugar and nonalcoholic fatty liver disease (NAFLD).

The incidence of T2D and NAFLD are rising to epidemic proportions with recent worldwide figures reaching over 463 and 62 million people, respectively, and it is well established that poor dietary and lifestyle habits are major causes of their development.

There is thus a need to find means of reducing hepatic triglycerides and/or improving glucose metabolism, particularly to prevent or treat NAFLD and T2D.

SUMMARY OF THE INVENTION

The present invention arises from the unexpected discovery, by the Inventors, that oral administration of yogurt that contains branched chain amino acid (BCAAs) metabolites correlated with reduction of hepatic triglycerides and improvement in glucose metabolism and insulin sensitivity.

In particular the Inventors showed that yogurt intake impacts the hepatic metabolome, notably increasing the levels of branched chain hydroxy acids (h-BCAAs or BCHA) which correlate with improved metabolic parameters. These BCAA metabolites are generated upon milk fermentation and concentrated in yogurt. Interestingly, diet-induced obesity reduces plasma and tissue levels of h-BCAAs and this is partly prevented by dietary yogurt intake. Furthermore, the Inventors showed that h-BCAAs improve insulin action on glucose metabolism in liver and muscle cells, identifying h-BCAAs as cell-autonomous metabolic regulators and potential mediators of yogurt's health effects.

Thus, the present invention relates to branched chain amino acid metabolites or a composition comprising branched chain amino acid metabolites for use in reducing hepatic triglycerides and/or improving glucose metabolism.

In embodiments the present invention provides branched chain amino acid metabolites or a composition comprising branched chain amino acid metabolites for use in reduction of hepatic triglycerides, glycemia (preferably fasting glucose) and/or insulinemia (preferably fasting insulin).

The present invention also relates to the use of a composition comprising branched chain amino acid metabolites for reducing hepatic triglycerides and/or improving glucose metabolism.

In embodiments the invention provides branched chain amino acid metabolites or a composition comprising branched chain amino acid metabolites for use in treatment or prevention of insulin resistance, diabetes in particular T2D, hepatic steatosis and/or (NAFLD).

In another aspect, the present invention also relates to a method for reducing hepatic triglycerides and/or improving glucose metabolism by administering to an individual in need thereof branched chain amino acid metabolites or a composition comprising branched chain amino acid metabolites.

In another aspect, the present invention also relates to the use of branched chain amino acid metabolites or a composition comprising branched chain amino acid metabolites for the manufacture of a dietary supplement or a medication for reducing hepatic triglycerides and/or improving glucose metabolism.

As used herein the term "dietary supplement" shall be taken to mean a product that is intended to be ingested in addition to the normal diet of a subject for nutritional purposes and/or to provide health benefits such as the prevention or treatment of diseases or disorders.

As used herein the term "probiotic supplement" shall be taken to mean a dietary supplement comprising probiotic species for the purposes of dietary probiotic supplementation.

As intended herein, the expression "x % (w/w)" is considered equivalent to "x g per 100 g".

As used herein the term "at least" also includes the starting point of the open range. For example, an amount of "at least 95.00% w/w" means any amount equal to 95.00 percentage by weight or above.

As used herein the term "about" defines a range of plus or minus 10% of the cited value. For example, an amount of "about 20 weight %" means any amount within the range of 18 to 22 weight %.

As intended herein the term "dairy composition" relates to a milk-based composition suitable for animal consumption, in particular human consumption.

As used herein the term "HICA" shall be taken to refer to alpha-hydroxyisocaproic acid.

As used herein the term "HIVA" shall be taken to refer to alpha-hydroxyisovaleric acid.

As used herein the term "HMVA" shall be taken to refer to 2-hydroxy-3-methylvaleric acid.

As used herein the term "h-BCAA" refers to hydroxy metabolites of branched chain amino acids (i.e. branched chain hydroxy acids or "BCHA") and shall be taken to collectively refer to HICA, HIVA and HMVA, along with enantiomers, racemic mixtures, salts, esters or hydrates thereof.

"Diet-induced body weight gain" and "diet-induced insulin resistance" are defined herein as body weight gain and insulin resistance resulting from an excessive dietary intake, including an excessive dietary intake of fat, in particular unsaturated fat, and optionally an excessive dietary intake of simple sugars, including sucrose and fructose. For a given subject, an excessive dietary intake, in particular of fat and optionally of simple sugars, refers to the consumption of an amount of diet, in particular of fat and optionally of simple sugars, higher than the amount necessary to meet the physiological needs and maintain the energy balance of said subject. The effect of a treatment on reduction of—or prevention—of diet-induced body weight gain and insulin resistance in a subject can be assessed by comparing body weight gain and insulin resistance observed in a subject receiving the treatment with those observed in the same subject without treatment receiving the same diet and having the same level of physical activity.

As used herein, "decreasing the body weight gain" means limiting, lowering or reducing the enhancement of body weight induced by a given diet as defined above in a subject by comparison to the enhancement of body weight induced by said given diet in said subject but who would not consume the h-BCAAs according to the invention.

As used herein, "improving the insulin resistance" means ameliorating or decreasing the level of insulin resistance induced by a given diet as defined above in a subject by comparison to the level of insulin resistance induced by said given diet in said subject but who would not consume the h-BCAAs according to the invention.

Tests for evaluating insulin resistance in a subject are known in the art. The level of insulin resistance in a subject can be measured with any insulin resistance test known in the art, such as the homeostatic model assessment of insulin resistance (HOMA-IR) or more classically by the gold-standard hyperinsulinemic-euglycemic clamp procedure.

In a preferred embodiment of the present invention, the body weight gain and insulin resistance are induced by (i.e., associated to) a high fat diet (HFD) in said subject.

In a preferred embodiment of the present invention, the body weight gain and insulin resistance are induced by (i.e., associated to) a high sucrose diet (HS) in said subject.

In a preferred embodiment of the present invention, the body weight gain and insulin resistance are induced by (i.e., associated to) a high fat high sucrose diet (HFHS) in said subject.

As used herein the term "glucose metabolism" shall be taken to include glucose homeostasis, glucose management or insulin sensitivity.

DETAILED DESCRIPTION OF THE INVENTION

The present invention provides branched chain amino acid metabolites for use in reducing hepatic triglycerides and/or improving glucose metabolism.

Preferably said branched chain amino acid metabolites are h-BCAAs. Preferably said h-BCAAs are selected from the group consisting of HICA, HIVA, HMVA and combinations thereof. In a most preferred embodiment said h-BCAAs are the combination of HICA, HIVA and HMVA. In embodiments of the uses or methods according to the present invention said h-BCAAs are a lactic acid bacteria metabolite of dairy milk fermentation.

In embodiments the invention provides branched chain amino acid metabolites for use in reduction of hepatic triglycerides, glycemia (preferably fasting glucose), insulinemia (preferably fasting insulin).

Accordingly in one embodiment the present invention provides a composition comprising branched chain amino acid metabolites for use in reducing hepatic triglycerides and/or improving glucose metabolism, preferably glycemia (preferably fasting glucose), insulinemia (preferably fasting insulin).

In embodiments the invention provides branched chain amino acid metabolites for use in treatment or prevention of insulin resistance, diabetes in particular T2D, hepatic steatosis and/or non-alcoholic fatty liver disease.

Individual

The "individual" according to the invention is a mammal, preferably a human. The individual according to the invention may be obese or overweight and/or suffer from a disease or disorder such as insulin resistance, pre-diabetes, diabetes in particular T2D, hepatic steatosis (i.e. lipid accumulation in liver) and/or non-alcoholic fatty liver disease. In embodiments the individual has diet-induced body weight gain and/or diet-induced insulin resistance.

In embodiments the individual has high fat diet-induced body weight gain and/or high fat diet-induced insulin resistance. In embodiments the individual has high sucrose diet-induced body weight gain and/or high sucrose diet-induced insulin resistance. In embodiments the individual has HFHS diet-induced body weight gain and/or HFHS diet-induced insulin resistance.

In embodiments the invention provides branched chain amino acid metabolites for use in reducing hepatic triglycerides and/or improving glucose metabolism.

In embodiments the invention provides branched chain amino acid metabolites for use in reduction of hepatic triglycerides, glycemia (preferably fasting glucose), insulinemia (preferably fasting insulin).

In embodiments the invention provides branched chain amino acid metabolites for use in treatment or prevention of insulin resistance, diabetes in particular T2D, hepatic steatosis and/or non-alcoholic fatty liver disease.

Preferably said branched chain amino acid metabolites are h-BCAAs. Preferably said h-BCAAs are selected from the group consisting of HICA, HIVA, HMVA and combinations thereof. In a most preferred embodiment said h-BCAAs are the combination of HICA, HIVA and HMVA. In embodiments of the uses or methods according to the present invention said h-BCAAs are a lactic acid bacteria metabolite of dairy milk fermentation.

In embodiments, the branched chain amino acid metabolites are administered to or consumed by an individual in the form of a food composition, a nutraceutical composition, dietary supplement, probiotic supplement or a nutritional composition.

In embodiments, the branched chain amino acid metabolites are administered to or consumed by an individual in the form of a dairy composition, more preferably a milk or a yogurt.

In embodiments, the branched chain amino acid metabolites are in a composition at a total concentration from 0.1 μM to 1 mM, preferably from 0.1 μM to 10 μM, more preferably from 0.1 μM to 1 μM.

In embodiments, the branched chain amino acid metabolites are in a composition at a total concentration of at least 0.1 μM, 0.5 μM, 1 μM, 5 μM, 10 μM, 50 μM, 100 μM, 500 μM or 1 mM.

In embodiments, HICA is present in a composition at a concentration of at least 0.1 μM, 0.5 μM, 1 μM, 5 μM, 10 μM, 50 μM, 100 μM, 500 μM or 1 mM.

In embodiments, HIVA is present in a composition at a concentration of at least 0.1 μM, 0.5 μM, 1 μM, 5 μM, 10 μM, 50 μM, 100 μM, 500 μM or 1 mM.

In embodiments, HMVA is present in a composition at a concentration of at least 0.1 μM, 0.5 μM, 1 μM, 5 μM, 10 μM, 50 μM, 100 μM, 500 μM or 1 mM.

In embodiments, the branched chain amino acid metabolites are present in a composition as mixture of HICA, HIVA and HMVA at a total concentration of at least 0.1 μM, 0.5 μM, 1 μM, 5 μM, μM, 50 μM, 100 μM, 500 μM or 1 mM.

In embodiments, the branched chain amino acid metabolites are present in a composition as mixture of HICA, HIVA and HMVA at a concentration from 0.1 μM to 1 mM, preferably from 0.1 μM to 10 μM, more preferably from 0.1 μM to 1 μM.

In embodiments, the branched chain amino acid metabolites are administered to or consumed by the individual every week, preferably daily.

In embodiments, the branched chain amino acid metabolites are administered to or consumed by the individual at once.

Composition

The present invention provides a composition comprising branched chain amino acid metabolites for use in reducing hepatic triglycerides and/or improving glucose metabolism, in an individual. Preferably said branched chain amino acid metabolites are h-BCAAs. Preferably said h-BCAAs are selected from the group consisting of HICA, HIVA, HMVA and combinations thereof. In a most preferred embodiment said h-BCAAs are the combination of HICA, HIVA and HMVA. In embodiments of the uses or methods according to the present invention said h-BCAAs are a lactic acid bacteria metabolite of dairy milk fermentation.

In embodiments the invention provides a composition comprising branched chain amino acid metabolites for use in reduction of hepatic triglycerides, glycemia (preferably fasting glucose), insulinemia (preferably fasting insulin).

The composition according to the invention is suitable for consumption or ingestion, preferably by oral means. Accordingly, the composition comprises or consists essentially of comestible matter. It is particularly preferred that the compositions of the invention are substantially free of pathogenic or toxicogenic matter.

The composition according to the invention may be a pharmaceutical composition, a food composition, a nutraceutical composition, dietary supplement, probiotic supplement and/or a nutritional composition.

In embodiments the supplement is in the form of tablets, powder, capsules or any other form usually not associated with food. Where the composition according to the invention is a probiotic or dietary supplement it may also comprise acceptable excipients, flavouring agents, sweeteners, preservatives and/or emulsifiers.

Where the composition according to the invention is a pharmaceutical composition or dietary supplement it may also comprise at least one pharmaceutically acceptable excipient or vehicle.

Nutritional compositions which can be used according to the invention include dairy products, preferably fermented dairy products. The fermented products can be in the form of a liquid or in the form of a dry powder obtained by drying the fermented liquid. Examples of dairy products include fermented milk and or fermented whey in set, stirred or drinkable form, cheese and yoghurt. The fermented product can also be a fermented vegetable, such as fermented soy, cereals and/or fruits in set, stirred or drinkable forms. Nutritional compositions which can be used according to the invention also include baby foods, infant milk formulas and infant follow-on formulas. In a preferred embodiment, the fermented product is a fresh product. A fresh product, which has not undergone severe heat treatment steps, has the advantage that the bacterial strains present are in the living form.

Dairy Composition

Preferably, the composition according to the invention is a dairy composition, in particular a fermented dairy composition comprising branched chain amino acid metabolite.

Preferably said branched chain amino acid metabolites are h-BCAAs. Preferably said h-BCAAs are selected from the group consisting of HICA, HIVA, HMVA and combinations thereof. In a most preferred embodiment said h-BCAAs are the combination of HICA, HIVA and HMVA. In embodiments of the uses or methods according to the present invention said h-BCAAs are a lactic acid bacteria metabolite of dairy milk fermentation.

Preferably, the dairy composition according to the invention comprises or derives (in particular by fermentation) from a composition containing from 30 to 100% (w/w) milk, more preferably from 50 to 100% (w/w) milk and even more preferably from 70 to 100% (w/w) milk.

Preferably also, the dairy composition according to the invention comprises or derives (in particular by fermentation) from a composition essentially consisting of milk or consisting only of milk. As intended herein "milk" preferably relates to vegetal or animal milk.

Preferably, the dairy composition according to the invention comprises or derives (in particular by fermentation) from a composition comprising one or both of skimmed or non-skimmed milk. Preferably said milk or milks may be in liquid, powdered and/or concentrated form. In one embodiment said milk or milks may be enriched or fortified with further milk components or other nutrients such as but not limited to vitamins, minerals, trace elements or other micronutrients. Preferably, the dairy composition according to the invention is a fermented dairy composition, more preferably a fermented milk composition such as but not limited to a yogurt.

As intended herein, a "fermented dairy composition" is derived from a dairy composition according to the invention by the acidifying action of at least one lactic acid bacterium, which may be comprised in a ferment, inoculant, culture or starter. More preferably said dairy composition according to the invention is obtained by the acidifying action of at least one, two, three, four, five, six, seven or more lactic acid bacteria strains. Accordingly the "fermented dairy composition" comprises at least one, two, three, four, five, six, seven or more lactic acid bacteria strains.

The lactic acid bacterium according to the invention preferably belongs to an Aerococcaceae, Carnobacteriaceae, Enterococcaceae, Lactobacillaceae, Leuconostocaceae, Streptococcaceae or Bifidobacteriaceae family and more preferably to an *Aerococcus, Carnobacterium, Enterococcus, Lactobacillus, Lactococcus, Leuconostoc, Oenococcus, Pediococcus, Streptococcus, Tetragenococcus, Vagococcus, Weissella* or *Bifidobacterium* genus. More preferably, the lactic acid bacterium according to the invention belongs to a *Lactobacillus brevis, Lactobacillus buchneri, Lactobacillus casei, Lactobacillus curvatus, Lactobacillus delbruckei*, in particular *L. delbruckei* supsb. *bulgaricus* or *lactis, Lactobacillus diolivorans, Lactobacillus fermentum, Lactobacillus fructivorans, Lactobacillus helveticus, Lactobacillus hilgardii, Lactobacillus jensenii, Lactobacillus kunkeei, Lactobacillus mali, Lactobacillus nagelii, Lactobacillus paracasei*, in particular:

*L. paracasei* subsp. *paracasei, Lactobacillus plantarum, Lactobacillus vini, Lactobacillus rhamnosus, Streptococcus thermophilus, Streptococcus lactis, Streptococcus raffinolactis, Streptococcus cremoris, Bifidobacterium adolescentis, Bifidobacterium animalis, Bifidobacterium bifidum, Bifidobacterium breve, Bifidobacterium infantis, Bifidobacterium lactis*, or *Bifidobacterium longum* species.

One or more lactic acid bacteria can be used for obtaining a fermented dairy composition according to the invention. Thus, in a preferred embodiment, a plurality of species of lactic acid bacteria comprising of *Streptococcus thermophilus* and *Lactobacillus delbrueckii* subsp. *bulgaricus* is used for obtaining a fermented dairy composition according to the invention. In a further embodiment, bacteria comprising of *Streptococcus thermophilus, Lactobacillus delbrueckii* subsp. *bulgaricus, Bifidobacterium* and *Lactococcus* are used for obtaining a fermented dairy composition according to the invention. Accordingly in one embodiment the invention provides a fermented dairy composition comprising of *Streptococcus thermophilus* and *Lactobacillus delbrueckii* subsp. *bulgaricus*, which in a further embodiment may additionally comprise *Bifidobacterium* and *Lactococcus* bacteria.

In a preferred embodiment, the lactic acid bacterium is a probiotic bacterium.

The expressions "fermented milk" and "yogurt" have the usual meanings attributed to them and may in appropriate circumstances be used interchangeably, e.g. a fermented dairy composition comprising *Lactobacillus bulgaricus, Streptococcus thermophilus* and further additional bacteria (e.g. probiotic strains) may be referred to as a "fermented milk" or alternatively as "yogurt".

Methods for the preparation of fermented milk products, such as yogurts or equivalents thereof, are well-known in the art. Typically a fermented milk product is prepared by culture of heat-treated (e.g. pasteurized) skimmed and/or non-skimmed milks with suitable microorganisms to provide a reduction in pH. The selection of suitable microorganisms (e.g. thermophilic lactic acid bacteria) is within the scope of the skilled person and for the preparation of yogurt will typically include *Lactobacillus bulgaricus* (also referred to as *Lactobacillus delbruckei* subsp. *bulgaricus*) and *Streptococcus thermophilus*, optionally with additional microorganisms such as but not limited to probiotic species or other species that may provide desirable organoleptic qualities to the composition.

The dairy composition, in particular the fermented dairy composition, according to the invention, may optionally further comprise secondary ingredients such as fruits, vegetables, nutritive and non-nutritive sweeteners, cereals, flavours, starch, thickeners, preservatives or stabilizers. Preferably the dairy composition, in particular the fermented dairy composition, according to the invention shall comprise up to about 30% (w/w) of said secondary ingredients, e.g. up to about 10%, 15%, 20%, 25% (w/w).

Preferably the dairy composition according to the invention is a fermented dairy composition, more preferably a fermented milk composition that comprises, comprises essentially or consists of milk that has been subjected to heat treatment at least equivalent to pasteurization, preferably said heat treatment is carried out prior to the preparation of the dairy composition or fermented dairy composition.

Preferably the dairy composition according to the invention is a fermented dairy composition, more preferably a fermented milk composition that comprises above about 0.3 g per 100 g by weight free lactic acid, more preferably the invention provides a fermented milk composition comprising above about 0.7 g or 0.6 g per 100 g by weight free lactic acid. Preferably the dairy composition according to the invention is a fermented dairy composition, more preferably a fermented milk composition that comprises a protein content at least equivalent to that of the milk or milks from which it is derived.

Preferably the dairy composition according to the invention is a fermented dairy composition, more preferably a fermented milk composition that has a pH equal to or lower than 5, more preferably between about 3.5 and about 4.5.

Preferably the dairy composition according to the invention is a fermented dairy composition, more preferably a fermented milk composition that has a viscosity lower than 200 mPa·s, more preferably lower than 100 mPa·s and most preferably lower that 60 mPa·s, at 10° C., at a shear rate of 64 $s^{-1}$. In one embodiment the dairy composition according to the invention is a drinkable fermented dairy composition, more preferably a fermented milk drink such as but not limited to a yogurt drink, kefir etc. In an alternative embodiment the dairy composition according to the invention is a fermented dairy composition, more preferably a fermented milk composition that is spoonable. As used herein the term "spoonable" shall be taken to mean a solid or semi-solid that may be consumed by means of a spoon or other utensil.

Preferably also, the dairy composition, in particular the fermented dairy composition, according to the invention, or the product according to the invention, may be stored at a temperature of from 1° C. to 10° C.

A single serving portion of the dairy composition, in particular the fermented dairy composition according to the invention, more preferably a fermented milk composition or the product according to the invention is preferably about 50 g, 60 g, 70 g, 75 g, 80 g, 85 g, 90 g, 95 g, 100 g, 105 g, 110 g, 115 g, 120 g, 125 g, 130 g, 135 g, 140 g, 145 g, 150 g, 200 g, 300 g or 320 g or alternatively about 1 oz, 2 oz, 3 oz, 4 oz, 5 oz, 6 oz or 12 oz by weight.

Preferably, the dairy composition, in particular the fermented dairy composition according to the invention, more preferably a fermented milk composition according to the invention comprises at least $10^6$, more preferably at least $10^7$ and most preferably at least $10^1$ colony forming unit (CFU) of *Lactobacillus bulgaricus* (also referred to as *Lactobacillus delbruckei* subsp. *bulgaricus*) and *Streptococcus thermophilus*, according to the invention per gram (g) of composition according to the invention e.g. at least of $5\times10^6$ *Lactobacillus bulgaricus* and $5\times10^6$ *Streptococcus thermophilus*. Preferably also the composition according to the invention comprises up to about $10^{11}$, more preferably at least $10^{10}$ and most preferably at least 109 colony forming unit (CFU) of *Lactobacillus bulgaricus* (also referred to as *Lactobacillus delbruckei* subsp. *bulgaricus*) and *Streptococcus thermophilus* bacteria per gram (g) of composition according to the invention.

Methods for the preparation of fermented milk products, such as yogurts or equivalents thereof, are well-known in the art. Typically a fermented milk product is prepared by culture of heat-treated (e.g. pasteurized) skimmed and/or non-skimmed milks with suitable microorganisms to provide a reduction in pH. The selection of suitable microorganisms (e.g. thermophilic lactic acid bacteria) is within the scope of the skilled person and for the preparation of yogurt will typically include *Lactobacillus bulgaricus* (also referred to as *Lactobacillus delbruckei* subsp. *bulgaricus*) and *Streptococcus thermophilus*, optionally with additional microorganisms such as but not limited to probiotic species and/or other species that may provide desirable organoleptic qualities to the composition. Fermented milk products may be either or set or stirred subsequent to fermentation.

Methods

The present invention also provides a method for reducing hepatic triglycerides and/or improving glucose metabolism, to an individual in need thereof, comprising administering an effective amount of a composition comprising branched chain amino acid metabolites to the individual.

In embodiments the invention methods for treatment or prevention of insulin resistance, diabetes, in particular T2D, hepatic steatosis, and/or non-alcoholic fatty liver disease in individuals in need thereof.

Preferably said branched chain amino acid metabolites are h-BCAAs. Preferably said h-BCAAs are selected from the group consisting of HICA, HIVA, HMVA and combinations thereof. In a most preferred embodiment said h-BCAAs are the combination of HICA, HIVA and HMVA. In embodiments of the uses or methods according to the present invention said h-BCAAs are a lactic acid bacteria metabolite of dairy milk fermentation.

DESCRIPTION OF THE FIGURES

FIG. 2. (A) HGP of FAO cells treated with a 1 mM mixture of HICA:HIVA:HMVA at molar ratio 1:1:0.5 in basal condition. (B) HGP of FAO cells treated with a 1 mM mixture of HICA:HIVA:HMVA at molar ratio 1:1:0.5 in insulin condition. (C) HGP of FAO cells treated with 0.5 and 1 mM of HICA, leucine or combination of both in basal condition. (D) HGP of FAO cells treated with 0.5 and 1 mM of HICA, leucine or combination of both in insulin condition. (E) Glucose uptake of L6 muscle cells treated with a 0.1 or 1 μM mixture of HICA:HIVA:HMVA at molar ratio 1:1:0.5 in basal condition. (F) Glucose uptake of L6 cells treated with a 0.1 or 1 μM mixture of HICA:HIVA:HMVA at molar ratio 1:1:0.5 in insulin condition. (G) Glucose uptake of L6 cells treated with 0.01, 0.1 or 1 μM of HICA in basal condition. (H) Glucose uptake of L6 cells treated with 0.01, 0.1 or 1 μM of HICA in insulin condition.*p<0.05 versus control, p<0.01 versus control, *p<0.001 vs control, kp<0.05 versus Leu 0.5 mM, $^{\$}$ p<0.05 versus Leu 1 mM, $^{\$\$}$ p<0.01 versus Leu 1 mM, $^{\$\$\$}$ p<0.001 versus Leu 1 mM. For panel C, D, G, H expressed in fold, basal and basal insulin are considered as a reference and represented by a dash line.

EXAMPLES

Figure 1:
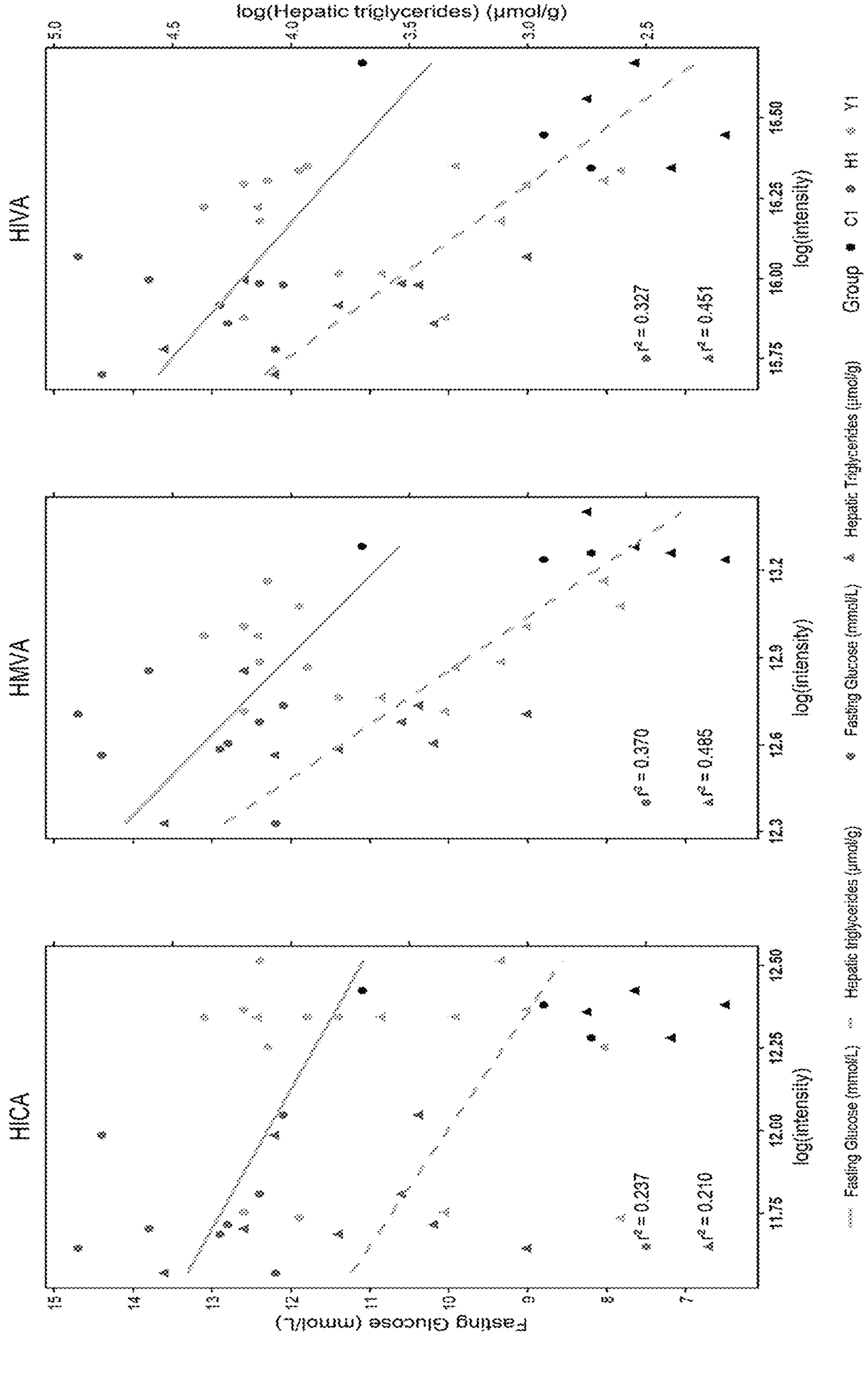
FIG. 1. Correlations between each hepatic BCHA levels and metabolic parameters, i.e., fasting glucose (trend curve in solid grey line) and hepatic triglycerides (trend curve in dash grey line). n=4-8. C1: low-fat low-sucrose control diet; H1: high-fat high sucrose diet with a protein mixture replacing casein; Y1: lyophilized yogurt incorporated in H diet.

Background and Aims:

Epidemiological studies indicate that yogurt intake is associated with reduced incidence of diabetes (T2D). However, the mechanism by which yogurt consumption may prevent T2D is unclear. The Inventors investigated the effect and mode of action of yogurt consumption to reduce the development of insulin resistance and T2D in a mouse model fed high-fat high-sucrose diet that contains a protein mixture representative of US diet (HFHS-PM).

Materials and Methods:

Yogurt was lyophilized and incorporated into the HFHS-PM diet (HFHS-PM+LYP; 4.8 kcal/g) representing 8% of daily energy intake. The control group was kept on the HFHS-PM diet (4.8 kcal/g). A group of mice was also fed a low-fat low sucrose diet (LFLS-PM; 3.7 kcal/g) and used as a healthy reference. Three independent experiments were performed to measure glucose homeostasis and insulin resistance using either oral glucose tolerance tests and glucose-stimulated insulin response, or tracer-coupled hyperinsulinemic euglycemic clamps to determine whole-body insulin sensitivity as well as hepatic and peripheral tissue insulin action.

Cell Culture and Hepatic Glucose Production

FAO rat hepatocytes were maintained in RPMI 1640 medium (Invitrogen) supplemented with 10% FBS. Cells were maintained in this medium 48 h before treatment. They were then serum-deprived overnight for 16 h with or without insulin (1 nM) and with HICA, HIVA or HMVA product at 10 nM, 100 nM, 1 μM, 10 μM, 100 μM and 1 mM. The cells were washed three times with PBS and incubated with phenol red- and glucose-free DMEM medium supplemented with 20 mM sodium L-lactate and 2 mM sodium pyruvate for 5 h with or without insulin and the indicated study treatment. Cell supernatant was collected, and glucose concentration was measured with the Amplex-Red Glucose assay kit accordingly to the manufacturer's instructions (Invitrogen). Cells were lysed with 50 mM NaOH, and protein concentration was determined using a BCA protein assay kit to normalize glucose production.

Results:

The Inventors found that yogurt intake at 12 weeks improves glucose homeostasis in HFHS-PM fed mice, as shown by reduced fasting glucose (234 mice, −0.7 mmol/I mean difference, 95% Cl: −1.05 to −0.28, two-sided Student t-test p<0.001) and insulin levels (235 mice, 0.79 mean ratio of log-transformed data, 95% Cl: 0.69 to 0.93, p=0.006, pooled summary analysis of three experiments). Single clamp study further validated that yogurt improves insulin sensitivity (52 mice; glucose infusion rate+3.6 mg/min/kg, p=0.02) and that the liver was the main site of improved glucose metabolism (52 mice; endogenous glucose production −1.9 mg/min/kg, p=0.06). Yogurt consumption also reduced hepatic steatosis.

Interestingly, the Inventors then found an impact of yogurt intake on the hepatic metabolome, revealing a novel inverse correlation between levels of many branched chain amino acid metabolites and hepatic triglycerides, fasting insulin and fasting glucose. BCHA were associated inversely with fasting glucose, fasting insulin and hepatic triglycerides. These BCAA metabolites were present in yogurt and generated upon milk fermentation.

In order to determine the biological role of h-BCAA in the preventive effect of yogurt, the correlation of their hepatic abundance with relevant metabolic parameters was analyzed.

An inverse correlation between BCHA hepatic levels and fasting glucose was found (HICA $r^2$=0.237, p=0.035; HMVA $r^2$=0.370, p=0.016; HIVA $r^2$=0.327, p=0.016), as well as hepatic triglyceride content (HICA $r^2$=0.210, p=0.042; HMVA $r^2$=0.485, p=0.002; HIVA $r^2$=0.451; p=0.002) (FIG. 1). In addition, a trend for an inverse association between hepatic HMVA and HIVA and fasting insulin was observed (HMVA $r^2$=0.177 p=0.097; HIVA $r^2$=0.255, p=0.070). Interestingly, HICA, HMVA and HIVA fall within the metabolism of branched chain amino acid (BCAA) as they are derived from leucine, isoleucine and valine, respectively.

The Inventors found BCHA to be reduced in H-fed obese mice and increased by yogurt treatment in the liver and to a lesser extent in skeletal muscle of H-fed animals. The Inventors elected to test the hypothesis that BCHA could exert direct effects in relevant cells. First, using FAO hepatic and L6 muscle cells, the Inventors investigated the effect of BCHA on hepatic glucose production (HGP) and glucose uptake, respectively. The Inventors found that a mixture of HICA:HIVA:HMVA used at 1 mM and at their relative ratio as in the lyophilized yogurt product reduced both basal glucose production and increased the suppressive effect of insulin in FAO cells (FIGS. 2A and B). Furthermore, HICA dose-dependently inhibited basal and insulin-suppressed HGP and competed the effect of its BCAA leucine precursor on this metabolic process (FIGS. 2C and D). Furthermore, the Inventors found that the BCHA mixture used at 0.1-1 μM concentrations to match their plasma levels in yogurt treated mice also increased glucose uptake in L6 myocytes (FIGS. 2E and F), and that these effects appeared to be mostly explained by HICA as determined from studies using individual BCHA (FIGS. 2G and H).

Overall, the in vitro studies provide mechanistic evidence that BCHA, and especially HICA, are cell-autonomous modulators of liver glucose production and muscle glucose uptake.

The invention claimed is:

1. A method for reducing hepatic triglycerides and/or improving glucose metabolism in an individual, comprising administering branched chain amino acid metabolites or a composition comprising branched chain amino acid metabolites to the individual, wherein said branched chain amino acid metabolites are alpha-hydroxyisocaproic acid (HICA), alpha-hydroxyisovaleric acid (HIVA), 2-hydroxy-3-methylvaleric acid (HMVA), or mixtures thereof.

2. The method according to claim 1, wherein said individual is obese or overweight.

3. The method according to claim 1, wherein said composition is a pharmaceutical composition, a nutraceutical composition, dietary supplement, probiotic supplement and/or a nutritional composition.

4. The method according to claim 1, wherein said composition is a food composition.

5. The method according to claim 1, wherein said individual has diet-induced body weight gain and/or diet-induced insulin resistance.

6. The method according to claim 1, wherein said individual suffers from insulin resistance, pre-diabetes, diabetes, hepatic steatosis and/or non-alcoholic fatty liver disease.

7. The method according to claim 1, wherein said method comprises administering HICA, HIVA, and HMVA.

8. The method according to claim 1, wherein said method comprises administering a yogurt comprising HICA, HIVA, and HMVA.

9. The method according to claim 1, wherein the branched chain amino acid metabolites are in a composition at a total concentration from 0.1 μM to 1 mM.

10. A method for reducing hepatic triglycerides and/or improving glucose metabolism in an individual, comprising (i) selecting an individual in need of reducing hepatic triglycerides and/or improving glucose metabolism; and (ii) administering branched chain amino acid metabolites or a composition comprising branched chain amino acid metabolites to the individual, wherein said branched chain amino acid metabolites are alpha-hydroxyisocaproic acid (HICA), alpha-hydroxyisovaleric acid (HIVA), 2-hydroxy-3-methylvaleric acid (HMVA), or mixtures thereof.

* * * * *